(12) United States Patent
Iglesias et al.

(10) Patent No.: US 11,426,625 B2
(45) Date of Patent: Aug. 30, 2022

(54) SYSTEM AND METHOD FOR OPTIMIZING PELVIC FLOOR MUSCLE TRAINING

(71) Applicant: Remendium Labs LLC, Baton Rouge, LA (US)

(72) Inventors: Ramon Jose Iglesias, DeLeon Springs, FL (US); David J. Mishelevich, Playa del Rey, CA (US); Sean C. Nash, Lake Forest, CA (US); Kaitlin B. Schaefer, San Clemente, CA (US); Jahnavi Lokre, Irvine, CA (US); Milan V. Trcka, North Tustin, CA (US); Himanshu Patel, Rancho Santa Margarita, CA (US); Jan B. Zwierstra, San Pedro, CA (US); Trevor Dunlop, Long Beach, CA (US); Aaron Gifford, Lake Elsinore, CA (US)

(73) Assignee: REMENDIUM LABS LLC, Baton Rouge, LA (US)

( * ) Notice: Subject to any disclaimer, the term of this patent is extended or adjusted under 35 U.S.C. 154(b) by 0 days.

(21) Appl. No.: 15/109,807

(22) PCT Filed: Jan. 6, 2015

(86) PCT No.: PCT/US2015/010356
§ 371 (c)(1),
(2) Date: Jul. 5, 2016

(87) PCT Pub. No.: WO2015/103629
PCT Pub. Date: Jul. 9, 2015

(65) Prior Publication Data
US 2016/0346610 A1   Dec. 1, 2016

Related U.S. Application Data

(60) Provisional application No. 61/923,997, filed on Jan. 6, 2014.

(51) Int. Cl.
*A63B 24/00* (2006.01)
*H04W 4/80* (2018.01)
(Continued)

(52) U.S. Cl.
CPC ............ *A63B 23/20* (2013.01); *A61B 5/1107* (2013.01); *A61B 5/227* (2013.01); *A61B 5/4337* (2013.01);
(Continued)

(58) Field of Classification Search
CPC . A63B 24/0062; A63B 23/20; A63B 2220/40; H04W 4/008; G09B 5/02;
(Continued)

(56) References Cited

U.S. PATENT DOCUMENTS

| 3,854,476 A | 12/1974 | Dickinson, III et al. |
| 2,830,582 A | 5/1987 | Ljung |

(Continued)

FOREIGN PATENT DOCUMENTS

| CA | 2862928 A1 | 8/2013 |
| DE | 103 45 282 B3 | 4/2005 |

(Continued)

OTHER PUBLICATIONS

US 9,248,265 B2, 02/2016, Haessler (withdrawn)
(Continued)

*Primary Examiner* — Sundhara M Ganesan
*Assistant Examiner* — Shila Jalalzadeh Abyaneh
(74) *Attorney, Agent, or Firm* — Clark & Elbing LLP

(57) ABSTRACT

A system and method for optimizing a patient's Kegel exercises is provided. The system includes a user interface device and a vaginal device. The vaginal device includes an intra-vaginal probe having an accelerometer that is configured to generate a signal in response to movement of the probe. The user interface device is connected to the vaginal probe. The user interface device is connected to the vaginal (Continued)

device and analyzes signals from the accelerometer to provide physiological feedback information to the patient. The vaginal device may be connected to the user interface device via wireless communications such as BLUETOOTH® or by wire. The user interface device may be a smart device or a computer that transmits information to central web-based data server accessible by the patient or authorized healthcare providers or third-party payers.

11 Claims, 11 Drawing Sheets

(51) Int. Cl.
| | |
|---|---|
| *A63B 23/20* | (2006.01) |
| *A61B 5/00* | (2006.01) |
| *A61B 5/22* | (2006.01) |
| *A61B 5/11* | (2006.01) |
| *G09B 5/02* | (2006.01) |
| *H04L 67/10* | (2022.01) |

(52) U.S. Cl.
CPC .......... *A61B 5/486* (2013.01); *A63B 24/0062* (2013.01); *G09B 5/02* (2013.01); *H04L 67/10* (2013.01); *H04W 4/80* (2018.02); *A61B 5/743* (2013.01); *A61B 2562/0219* (2013.01); *A63B 2220/40* (2013.01)

(58) Field of Classification Search
CPC ....... H04L 67/10; A61B 5/1107; A61B 5/486; A61B 5/4337; A61B 5/227; A61B 5/743
See application file for complete search history.

(56) References Cited

U.S. PATENT DOCUMENTS

| | | | |
|---|---|---|---|
| 4,669,478 A | 6/1987 | Robertson | |
| D309,866 S | 8/1990 | Fukuda et al. | |
| D310,275 S | 8/1990 | Su | |
| 5,328,077 A | 7/1994 | Lou | |
| 5,386,836 A | 2/1995 | Biswas | |
| 5,406,961 A | 4/1995 | Artal | |
| 5,562,717 A | 10/1996 | Tippey | |
| 5,603,685 A | 2/1997 | Tutrone, Jr. | |
| 5,674,238 A | 10/1997 | Sample | |
| 5,924,984 A | 7/1999 | Rao | |
| 6,001,060 A | 12/1999 | Churchill et al. | |
| 6,021,781 A | 2/2000 | Thompson | |
| 6,039,701 A | 3/2000 | Sliwa et al. | |
| 6,056,699 A | 5/2000 | Sohn et al. | |
| 6,080,118 A | 6/2000 | Blythe | |
| 6,086,549 A | 7/2000 | Neese | |
| 6,264,582 B1 * | 7/2001 | Remes .................. | A63B 23/20 482/8 |
| 6,272,371 B1 | 8/2001 | Shlomo | |
| D458,681 S | 6/2002 | Sherlock et al. | |
| 6,413,206 B2 | 7/2002 | Biswas | |
| 6,432,037 B1 | 8/2002 | Eini et al. | |
| 6,511,427 B1 | 1/2003 | Sliwa, Jr. et al. | |
| 6,672,996 B2 | 1/2004 | Ross et al. | |
| 6,679,854 B2 | 1/2004 | Honda et al. | |
| 6,741,895 B1 | 5/2004 | Gafni et al. | |
| D491,079 S | 6/2004 | Lim | |
| D491,274 S | 6/2004 | Dubniczki et al. | |
| 6,816,744 B2 | 11/2004 | Garfield et al. | |
| 7,079,882 B1 | 7/2006 | Schmidt | |
| 7,104,950 B2 | 9/2006 | Levy | |
| D535,203 S | 1/2007 | Chen | |
| D548,359 S | 8/2007 | Illein et al. | |
| 7,577,476 B2 | 8/2009 | Hochman et al. | |
| 7,608,037 B2 | 10/2009 | Levy | |
| 7,628,744 B2 | 12/2009 | Hoffman et al. | |
| 7,645,220 B2 | 1/2010 | Hoffman et al. | |
| 7,736,298 B2 | 6/2010 | Guerquin et al. | |
| 7,837,682 B2 | 11/2010 | Ostrovsky et al. | |
| 7,892,179 B2 | 2/2011 | Rieth | |
| 7,955,241 B2 | 6/2011 | Hoffman et al. | |
| 7,957,794 B2 | 6/2011 | Hochman et al. | |
| D651,531 S | 1/2012 | Rothman | |
| 8,147,429 B2 | 4/2012 | Mittal et al. | |
| 8,360,954 B2 * | 1/2013 | Kim .................. | A61B 5/202 482/113 |
| 8,623,004 B2 | 1/2014 | Johnson et al. | |
| 8,715,204 B2 | 5/2014 | Webster et al. | |
| 8,728,140 B2 | 5/2014 | Feemster et al. | |
| 8,740,767 B2 | 6/2014 | Rosen et al. | |
| 8,805,472 B2 | 8/2014 | Iglesias | |
| 8,821,407 B2 | 9/2014 | Kirsner | |
| 8,914,111 B2 | 12/2014 | Haessler et al. | |
| 8,983,627 B2 | 3/2015 | Pelger et al. | |
| 9,155,885 B2 | 10/2015 | Wei et al. | |
| D759,813 S | 6/2016 | Newman et al. | |
| D759,814 S | 6/2016 | Newman et al. | |
| 9,381,351 B2 | 7/2016 | Haessler | |
| 9,408,685 B2 | 8/2016 | Hou et al. | |
| 9,861,316 B2 | 1/2018 | Egorov | |
| 9,970,923 B2 | 5/2018 | Sturman et al. | |
| 9,974,635 B2 | 5/2018 | Rosen et al. | |
| D832,437 S | 10/2018 | Zeltwanger et al. | |
| D841,155 S | 2/2019 | McMenamin et al. | |
| D845,478 S | 4/2019 | Luke | |
| D846,120 S | 4/2019 | Wallis et al. | |
| D852,069 S | 6/2019 | Fu | |
| D853,035 S | 7/2019 | Moretti | |
| D855,825 S | 8/2019 | Parsons et al. | |
| 10,470,862 B2 | 11/2019 | Iglesias | |
| D888,949 S | 6/2020 | Beer et al. | |
| D889,649 S | 7/2020 | Beer et al. | |
| D893,026 S | 8/2020 | Leather | |
| D896,958 S | 9/2020 | Beer et al. | |
| D896,959 S | 9/2020 | Beer et al. | |
| D897,530 S | 9/2020 | Beer et al. | |
| D898,911 S | 10/2020 | Beer et al. | |
| D899,593 S | 10/2020 | Beer et al. | |
| D903,853 S | 12/2020 | Wiegerinck | |
| D903,896 S | 12/2020 | Tianhao et al. | |
| D908,160 S | 1/2021 | Sun | |
| D909,679 S | 2/2021 | Chen | |
| D910,851 S | 2/2021 | Lagrange et al. | |
| D918,390 S | 5/2021 | Ollivier | |
| D919,083 S | 5/2021 | Lee | |
| D923,806 S | 6/2021 | Bunger von Wurmb et al. | |
| D923,876 S | 6/2021 | Hasegawa | |
| 11,135,085 B2 | 10/2021 | Mikkonen et al. | |
| 2001/0001125 A1 | 5/2001 | Schulman et al. | |
| 2002/0022836 A1 | 2/2002 | Goble et al. | |
| 2002/0111586 A1 | 8/2002 | Mosel et al. | |
| 2003/0028180 A1 | 2/2003 | Franco | |
| 2004/0236223 A1 | 11/2004 | Barnes et al. | |
| 2004/0260207 A1 | 12/2004 | Eini et al. | |
| 2005/0148447 A1 | 7/2005 | Nady | |
| 2005/0177067 A1 | 8/2005 | Tracey et al. | |
| 2005/0256423 A1 | 11/2005 | Kirsner | |
| 2006/0036188 A1 | 2/2006 | Hoffman et al. | |
| 2006/0074289 A1 | 4/2006 | Adler et al. | |
| 2006/0084848 A1 | 4/2006 | Mitchnick | |
| 2006/0211911 A1 | 9/2006 | Jao et al. | |
| 2007/0066880 A1 | 3/2007 | Lee et al. | |
| 2007/0232882 A1 | 10/2007 | Glossop et al. | |
| 2007/0255090 A1 | 11/2007 | Addington et al. | |
| 2007/0265675 A1 | 11/2007 | Lund et al. | |
| 2007/0270686 A1 | 11/2007 | Ritter et al. | |
| 2008/0077053 A1 | 3/2008 | Epstein et al. | |
| 2008/0139876 A1 * | 6/2008 | Kim .................. | A61B 5/4337 600/29 |
| 2008/0146941 A1 | 6/2008 | Dala-Krishna | |
| 2008/0149109 A1 | 6/2008 | Ziv | |
| 2008/0154131 A1 | 6/2008 | Lee et al. | |
| 2008/0171950 A1 | 7/2008 | Franco | |
| 2008/0300658 A1 | 12/2008 | Meskens | |
| 2009/0024001 A1 * | 1/2009 | Parks .................. | A61B 5/227 600/300 |

(56) References Cited

U.S. PATENT DOCUMENTS

| | | |
|---|---|---|
| 2009/0149740 A1 | 6/2009 | Hoheisel |
| 2009/0216071 A1 | 8/2009 | Zipper |
| 2009/0270963 A1 | 10/2009 | Pelger et al. |
| 2009/0306509 A1 | 12/2009 | Pedersen et al. |
| 2010/0069784 A1 | 3/2010 | Blaivas |
| 2010/0174218 A1* | 7/2010 | Shim ............... A61B 5/224 601/84 |
| 2010/0222708 A1 | 9/2010 | Hitchcock et al. |
| 2010/0249576 A1 | 9/2010 | Askarinya et al. |
| 2010/0262049 A1 | 10/2010 | Novak et al. |
| 2011/0054357 A1 | 3/2011 | Egorov et al. |
| 2011/0077500 A1 | 3/2011 | Shakiba |
| 2011/0144458 A1* | 6/2011 | Gauta ............... A61B 5/7445 600/304 |
| 2011/0190580 A1* | 8/2011 | Bennett ............ A61B 1/00016 600/109 |
| 2011/0190595 A1* | 8/2011 | Bennett ............ A61B 17/42 600/301 |
| 2011/0196263 A1 | 8/2011 | Egorov et al. |
| 2012/0016258 A1 | 1/2012 | Webster et al. |
| 2012/0245490 A1* | 9/2012 | Fausett ............... A61B 5/11 600/595 |
| 2012/0265044 A1 | 10/2012 | Broens |
| 2012/0265049 A1 | 10/2012 | Iglesias |
| 2013/0035611 A1 | 2/2013 | White |
| 2013/0053627 A1 | 2/2013 | Bercovich et al. |
| 2013/0130871 A1* | 5/2013 | McCoy ............... A63B 23/20 482/113 |
| 2013/0144191 A1 | 6/2013 | Egorov et al. |
| 2013/0184567 A1* | 7/2013 | Xie ............... A61B 5/065 600/595 |
| 2013/0192606 A1 | 8/2013 | Ziv et al. |
| 2013/0237771 A1 | 9/2013 | Runkewitz et al. |
| 2013/0324380 A1 | 12/2013 | Horsley |
| 2014/0066813 A1 | 3/2014 | Daly et al. |
| 2014/0073879 A1 | 3/2014 | Cantor et al. |
| 2014/0088471 A1* | 3/2014 | Leivseth ............ A63B 23/20 601/89 |
| 2014/0155225 A1* | 6/2014 | Sedic ............... A61N 1/36007 482/9 |
| 2014/0213927 A1 | 7/2014 | Webster et al. |
| 2014/0296705 A1 | 10/2014 | Iglesias |
| 2014/0309550 A1 | 10/2014 | Iglesias |
| 2015/0032030 A1 | 1/2015 | Iglesias |
| 2015/0112230 A1 | 4/2015 | Iglesias |
| 2015/0112231 A1 | 4/2015 | Iglesias |
| 2015/0133832 A1 | 5/2015 | Courtion et al. |
| 2015/0196802 A1 | 7/2015 | Siegel |
| 2015/0282763 A1 | 10/2015 | Rosenshein |
| 2016/0008664 A1 | 1/2016 | Siegel |
| 2016/0022198 A1 | 1/2016 | De Laat |
| 2016/0051354 A1 | 2/2016 | Patankar et al. |
| 2016/0074276 A1 | 3/2016 | Scheuring et al. |
| 2016/0121105 A1 | 5/2016 | Lee et al. |
| 2016/0279469 A1 | 9/2016 | Rose |
| 2016/0346610 A1 | 12/2016 | Iglesias et al. |
| 2017/0281072 A1 | 10/2017 | Iglesias |
| 2017/0281299 A1 | 10/2017 | Iglesias |
| 2017/0291012 A1 | 10/2017 | Iglesias |
| 2017/0303843 A1 | 10/2017 | Iglesias |
| 2017/0312530 A1 | 11/2017 | Schilling et al. |
| 2017/0332959 A1 | 11/2017 | Bartlett |
| 2018/0021121 A1 | 1/2018 | Zeltwanger et al. |
| 2019/0133738 A1 | 5/2019 | Rosen et al. |
| 2019/0160332 A1 | 5/2019 | Beer et al. |
| 2020/0029812 A1 | 1/2020 | Govari et al. |
| 2020/0069161 A1 | 3/2020 | Schentag et al. |
| 2020/0405142 A1 | 12/2020 | Whitaker |
| 2021/0321983 A1 | 10/2021 | Miyamoto |

FOREIGN PATENT DOCUMENTS

| | | | |
|---|---|---|---|
| EP | 2 689 724 A1 | 1/2014 | |
| EP | 2689724 A1 | 1/2014 | |
| EP | 3366212 A1 | 8/2018 | |
| GB | 249754 A | 1/2013 | |
| JP | 2002-143133 A | 5/2002 | |
| JP | 2009-538176 A | 11/2009 | |
| JP | 2011-183167 | 9/2011 | |
| RU | 2307636 C1 | 10/2007 | |
| WO | WO 96/05768 | 2/1996 | |
| WO | WO-96/05768 A1 | 2/1996 | |
| WO | WO-99/05963 A1 | 2/1999 | |
| WO | WO-00/09013 A1 | 2/2000 | |
| WO | WO 0009013 A1 | 2/2000 | |
| WO | WO-00/23030 A1 | 4/2000 | |
| WO | WO-02/17987 A2 | 3/2002 | |
| WO | WO 2006107930 A2 | 10/2006 | |
| WO | WO-2007/136266 A1 | 11/2007 | |
| WO | WO 2010131252 A2 | 11/2010 | |
| WO | WO 2011050252 A1 | 4/2011 | |
| WO | WO 2011121591 A2 | 10/2011 | |
| WO | WO 2011159906 A2 | 12/2011 | |
| WO | WO 2012079127 A1 | 6/2012 | |
| WO | 2012/138232 A1 | 10/2012 | |
| WO | WO 2013082006 A1 | 6/2013 | |
| WO | WO 2013116310 A1 | 8/2013 | |
| WO | WO-2013116310 A1 * | 8/2013 | ........... A61B 5/4848 |
| WO | WO 2015103629 A1 | 7/2015 | |
| WO | WO 2016026914 A2 | 2/2016 | |
| WO | WO 2016042310 A1 | 3/2016 | |
| WO | WO 2016067023 A1 | 5/2016 | |
| WO | WO-2016/119002 A1 | 8/2016 | |
| WO | WO-2016/203485 A1 | 12/2016 | |
| WO | WO-2017/149688 A1 | 9/2017 | |
| WO | WO-2018/023037 A1 | 2/2018 | |
| WO | WO-2019/084468 A1 | 5/2019 | |
| WO | WO-2019/084469 A1 | 5/2019 | |
| WO | WO-2020/092343 A1 | 5/2020 | |

OTHER PUBLICATIONS

International Search Report and Written Opinion, dated Mar. 26, 2015, issued in International Application No. PCT/US2015/010356, filed on Jan. 6, 2015.

Extended European Search Report dated Aug. 16, 2017 issued in related EP Application No. 15733078.8. filed Aug. 2, 2016.

Rosenbaum, Talli Y. et al., "The Role of Pelvic Floor Physical Therapy in the Treatment of Pelvic and Genital Pain-Related Sexual Dysfunction", 2008, J. Sex Med, 5: pp. 513-523.

Glazer et al., "Pelvic floor muscle biofeedback in the treatment of urinary incontinence: A literature review.", Applied Psychophysiology and Biofeedback 31(3): 187-201 (2006).

Parekh et al., "The role of pelvic floor exercises on post-prostatectomy incontinence," J Urol. 170(1):130-33 (2003) (Abstract Only) (2 pages).

Moen et al., "Pelvic floor muscle function in women presenting with pelvic floor disorders," Int Urogynecol J Pelvic Floor Dysfunct. 20(7):843-6 (2009).

Kandadai et al., "Correct Performance of Pelvic Muscle Exercises in Women Reporting Prior Knowledge," Female Pelvic Med Reconstr Surg. 21(3):135-40 (2015).

Rosenblatt et al., "Interactive Pelvic Floor Muscle Training for Female Urinary Incontinence," Renovia, Inc., retrieved Apr. 30, 2019 from <https://renoviainc.com/wp-content/uploads/2018/04/REN005.01-White-Paper-12Apr18-FINAL.pdf> (2018) (6 pages).

Malcovati et al., Interface Circuitry and Microsystems. *MEMS–A Practical Guide to Design, Analysis, and Applications*. Jan G. Korvink and Oliver Paul, 901-942 (2006).

Rosenbaum et al., "The Role of Pelvic Floor Pysical Therapy in the Treatment of Pelvic and Genital Pain-Related Sexual Dysfunction," J Sex Med. 5(3): 513-23 (2008).

Rosenblatt et al., "Evaluation of an accelerometer-based digital health system for the treatment of female urinary incontinence: A pilot study," Neurourol Urodyn. 38(7): 1944-1952 (2019).

Nygaard et al., "Efficacy of pelvic floor muscle exercises in women with stress, urge, and mixed urinary incontinence," Am J Obstet Gynecol. 174(1 Pt 1):120-125 (1996) (Abstract only).

(56) References Cited

OTHER PUBLICATIONS

International Search Report and Written Opinion for International Application No. PCT/US2019/058527, dated Feb. 21, 2020 (18 pages).
Office Action for Japanese Patent Application No. 2019-504938, dated May 18, 2021 (10 pages).
International Search Report and Written Opinion for International Application No. PCT/US2021/033155, dated Aug. 25, 2021 (19 pages).
Communication pursuant to Article 94(3) EPC for European Patent Application No. 15733078.8, dated Aug. 24, 2021 (8 pages).
Office Action for Japanese Patent Application No. 2020-143711, dated Sep. 8, 2021 (4 pages).
First Examination Report for Australian Patent Application No. 2020281099, dated Nov. 2, 2021 (6 pages).
Office Action for Brazilian Patent Application No. BR112019001746-1, dated Dec. 10, 2021 (5 pages).
Extended European Search Report for European Patent Application No. 19793343.5, dated Jan. 27, 2022 (7 pages).
Notice of Preliminary Rejection for Korean Patent Application No. 10-2019-7005863, dated Jan. 26, 2022 (17 pages).
Office Action for Chinese Patent Application No. 201780060078.4, dated Jan. 17, 2022 (20 pages).
Office Action for Japanese Patent Application No. 2019-504938, dated Feb. 8, 2022 (13 pages).
Office Action for Chinese Patent Application No. 201880083895.6, dated Feb. 8, 2022 (24 pages).

* cited by examiner

SYSTEM AND METHOD FOR OPTIMIZING PELVIC FLOOR MUSCLE TRAINING

RELATED APPLICATIONS

This Application is a National Stage Application of PCT/US2015/10356, filed Jan. 6, 2015, which is related to and claims priority benefit of U.S. Application No. 61/923,997, filed Jan. 6, 2014, each of which are incorporated fully herein by reference for all purposes.

BACKGROUND OF THE INVENTION

The present invention relates to a system and method for optimizing Kegel exercises and more particularly, to a system and method for optimizing Kegel exercises using a device that measures a patient's performance of Kegel exercises and provides feedback to the patient.

Urinary incontinence is a prevalent condition in women that is associated with weakened pelvic floor muscles. Many common factors contribute to the weakening of the pelvic floor muscles in women such as pregnancy, childbirth, surgery, aging and weight gain. As the pelvic floor muscles weaken, women begin to suffer from urinary incontinence and experience related symptoms such as involuntarily leaking urine while sneezing, laughing or coughing. These symptoms are often uncomfortable, embarrassing and present personal hygiene issues for many women.

Various methods have been proposed to improve the strength and tone of the pelvic floor muscles. Dr. Arnold Kegel described pelvic floor exercises as a treatment option in urinary incontinence and invented a set of exercises, known as Kegel exercises to strengthen and support the pelvic floor. Kegel exercises are performed by repeatedly contracting and relaxing the pelvic floor muscles for a period of time. The repeated pelvic muscle contractions result in a stronger pelvic floor over time. Proper performance of Kegel exercises can provide for both the prevention and treatment of urinary incontinence, fecal incontinence, pelvic pain, and pelvic-organ prolapse. Proper performance of Kegel exercises can also result in the improvement of sexual experience.

Although Kegel exercises are an effective method to strengthen the pelvic floor, many women find it difficult to perform Kegel exercises correctly. Often women performing Kegel exercises simply do not know whether or not they are contracting the right muscles. Some women simply have problems identifying and contracting the right muscles. Some women may perform Kegel exercises incorrectly without even knowing that they are using the wrong muscles. Currently, there are not systems that measure a patient's performance with Kegel exercises or provide a patient with any feedback on their performance. If Kegel exercises are not done by engaging the right pelvic floor muscles, the patient may not achieve the maximum benefit, or any benefit, from performing the Kegel exercises.

Therefore, it would be advantageous to have a system and a method of optimizing Kegel exercises to achieve the maximum benefit from performing Kegel exercises and to address the above mentioned problems with Kegel exercises.

The present invention contemplates the real-time position and movement tracking described in International Patent Applications PCT/US2010/053712 and PCT/US2013/023806, and the multiple sensor-enable device described in International Patent Application PCT/US2012/066613, which are hereby incorporated in their entirety by reference.

In this regard, the real-time position and movement tracking may include sensing the position of the anatomical organ of interest to an anatomical reference point, such as the patient's pubic bone, the coccyx or the vagina, or to an external reference point, such as a target on a patient's garment or in the patient's surroundings. The method may be performed in real-time, for example, during a medical examination, procedure, or surgery. In another embodiment, the method may be performed at multiple time intervals. The multiple time intervals may occur, for example, pre- and post-event, wherein the event may be pregnancy or menopause.

The present invention may also be used to diagnose and treat pelvic organ prolapse (POP). Where the multiple sensor enabled device for vaginal insertion is capable of providing real-time data regarding the patient's physiology, the position and movement of the urethra, and the muscular strength of the patient's vagina and pelvic floor, this information may be used to treat and diagnose POP. The multiple sensor-enabled device may also provide pressure data, which reflects muscular strength, and provides a health care provider a detailed map of where the weakest anatomical points are for purposes of POP diagnosis and treatment. Where vaginal strengthening exercises are inadequate to prevent or relieve UI or POP, a surgeon would be able to use this information to target corrective procedures appropriately.

SUMMARY OF THE INVENTION

This invention is for a device for dynamically determining and displaying the position of the anterior wall of the vagina within the set of pelvic organs. It may consist of a set of MEMS accelerometer sensors, the positions of which show the profile of a flexible probe inserted into the vagina. The unique ability to display effects of the contracting pelvic muscles permits the proper training of patients in performing Kegel muscle contractions for prevention or mitigation of pelvic dysfunction including urinary incontinence, fecal incontinence, pelvic pain, and pelvic-organ prolapse. Proper Kegel training may also improve sexual experience. Temperature may be recorded as well.

The system may consist of the vaginal device, a cable from the vaginal device to an electronics box, a BLUETOOTH® wireless connection (a short-range radio wave communication) from the electronics box to a smart device such as an IPHONE®, IPOD®, or IPAD® (or ANDROID®- or WINDOWS®-based or other equivalents) for display and recording of results, with an Internet connection to a web server with a database. The data on this web server may be accessed with the correct authorization by the patient, their healthcare provider, or third party payers.

In addition to the training screens (dynamic-line profile or anatomical animation), the smart-device application may offer the user a history of her performance of up to a specified number of sessions as recorded on the smart device, and access to tour of the application, application settings, answers to Frequently Asked Questions, database web service, and other elements. A session is one set of maneuvers performed by a patient from the time she hits the Training button in the application to the time she hits the Stop button.

To work properly, the vaginal device must be inserted in the correct orientation so the MEMS accelerometers can work correctly. A line may be included on the vaginal device indicating how the device should be inserted. Additionally, the smart-device may display a screen showing the current orientation of the vaginal device and providing guidance of how to change to the proper orientation if the vaginal device is not positioned correctly.

Knowing the position of the vagina allows the healthcare professional to infer the likely position of related pelvic organs including the position of the urethra. As the vagina and the urethra are in close proximity and their relative location can be inferred from one another.

The contracting muscles are located near the entrance to the vagina or the introitus. In addition to the display of profile of the vaginal device, the temperature of the device slightly above the introitus may be displayed. The temperature reflects how hard the muscles are working. In another embodiment, pressure sensors may be included to measure and display the force of the muscle contractions.

The purpose of the device is to provide visual feedback to the patient to show whether the Kegel exercise is being performed correctly, and, if so, how effective the exercise is. With permission of the patient, the data can also be reviewed by healthcare professionals and third-party payers. In some situations, the performance of the patient and/or results (e.g., reduction of stress urinary incontinence) compared to initial performance may be used to assess outcomes and positively influence payments to physicians by third-party payers. It is also possible to have economic incentives for the patient. The display may be one or both indicating the actual movement and displaying the associated score.

In alternative embodiments, the feedback can be auditory in the form of voice, auditory in the form of a tone changing in magnitude, frequency, or both, or vibration changing in magnitude, frequency, or both. Voice feedback can include coaching, encouraging the patient to try harder during the performance of a Kegel exercise.

As the Kegel exercise is performed, the vaginal device lifts up and a line on the screen rotates from right to left indicated movement towards the front of the patient. The greater the lift, the more effective is the Kegel. The resultant score can be displayed in addition to or instead of the line position. Another display mode may be the relative position of the pelvic organs as an anatomical animated diagram. If the patient is performing the Kegel exercise incorrectly, the displayed line on the screen from the beginning of the exercise may rotate clockwise into a designated area on the screen as the patient bears down as she would do in a bowel movement. One of the key uses of the invention is to train the patient that such bearing down is incorrect if one wants to do a Kegel exercise. The line moving into the designated area, however, is not necessarily bad. When treating pelvic pain due to muscular contracture, a down movement of the device with a resultant clockwise rotation of the displayed line into the designated area on the screen would mean pelvic relaxation and its consequent descent.

The units of scoring may be Kegel power (kp). While in one embodiment scores are in the range of 0 to 100, other ranges can be used as well. At the beginning of their training, the muscles of many patients are weak. To provide encouragement, the application provides a zoom function so full deflection of the line is approximately 30 or 60 instead of 100. Therefore the line will move more providing positive feedback, although the score displayed is the same for any zoom level. Data from the Kegel training sessions are recorded on the smart device and data from the latest specific number (for example, 300) of sessions can be displayed on a history screen. In addition, session results are sent to the database on the web server. The information recorded and communicated can be just the highest score information including the time interval that the maximum level was held. Alternatively, the actual profile of the vaginal device as it changes can be transmitted. In addition, the temperature and pressure results, if any, are recorded, along with the start time and length of the session. Diary information can be collected by the patient on the smart device. That information can be uploaded to the web database server and viewed via web browser connection. The patient may also view prescription information entered by a healthcare professional on the central web database server.

BRIEF DESCRIPTION OF THE FIGURES

The invention will be described more in detail with reference to the following drawings.

FIG. 13 (B) is a view illustrating the Training Screen (Zoom 3 kp 024) of the present invention.

DETAILED DESCRIPTION OF THE INVENTION

Figure 1:
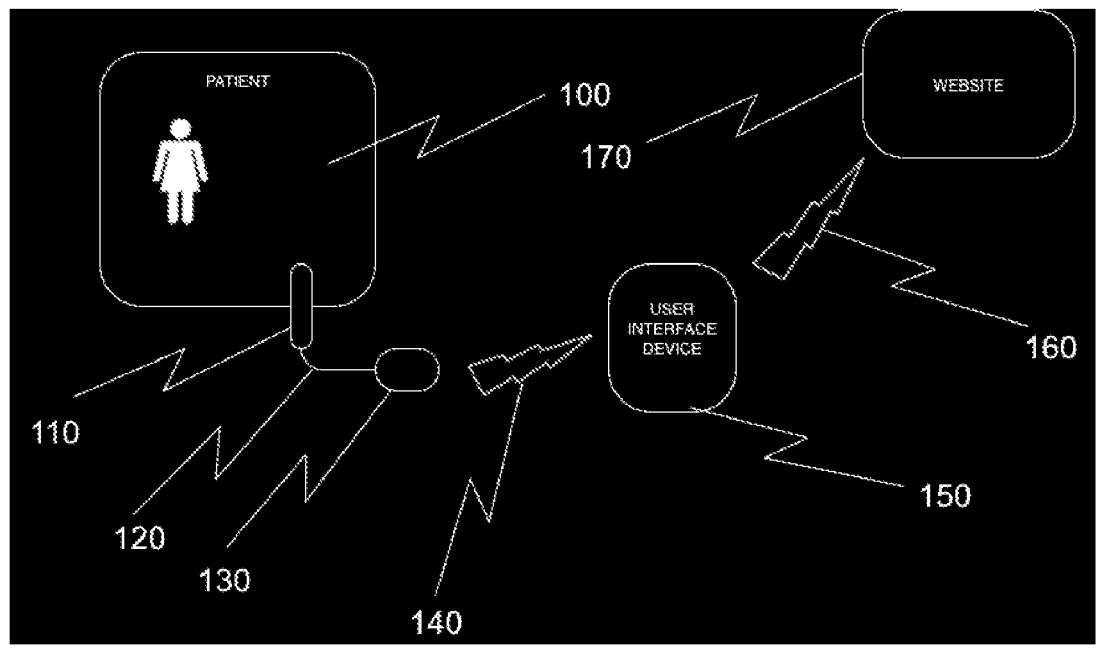
FIG. 1 shows a block diagram of the system of the present invention.

FIG. 1 shows a block diagram of the training system for the proper performance of Kegel exercises. The system includes a vaginal device 110 that is inserted into patient 100. The vaginal device 110 may be fabricated of silicone. Other suitable materials, however, may be used. The vaginal device 110 is connected via a cable 120 to an external electronics box 130. The external electronics box 130 may be connected by BLUETOOTH® connection 140 to a user interface device 150 that is a smart device such as an IPHONE®, an IPAD®, and IPOD® Touch, an ANDROID®-based system, a MICROSOFT® windows-based system, or other equivalent device. Alternatively, the external electronics box 130 may be connected to a custom display device. The user interface device 150 may communicate with a web-located central database server 170 via an internet connection 160. Data from the patient's sessions may be stored on the user interface device 150 and transmitted after each session to a central database server 170. The data transmitted may include the highest score plus the length of time maintaining that score, and possibly the raw data, and well as other data such as the start time of and the length of the session, maximum lift duration, the maximum temperature reached, and the maximum pressure reached. The BLUETOOTH® transmission from the external electronics box 130 to the user interface device 150 may be a serial data connection rather than the audio connection typical of BLUETOOTH® devices such as a BLUETOOTH® headset and the communication is handled through a Serial Port Protocol (SPP). If the smart device is from Apple, it requires that a special authentication chip (MFi chip where MFi means Made for iOS or Made for IPHONE®, IPAD®, IPOD®) is used in the embedded electronics in connection with the BLUETOOTH® connection.

The use of a smart device communicating using BLUETOOTH® with the external electronics box 130 is only one embodiment of the present invention. Alternatively other wireless means or even a wired connection may be used. In another embodiment, the output of the external electronics box 130 is processed using Lab VIEW or custom application running on a notebook or desktop computer with connection either wireless or wired.

The device may be used at home, work, physician's office, clinic, nursing home, pelvic health or other center or other locations suitable for the patient. A physician, nurse, technician, physical therapist, or central customer support may supply support for the patient. Central customer support may be provided even on a 24 hour, seven-day a week basis.

Figure 2:
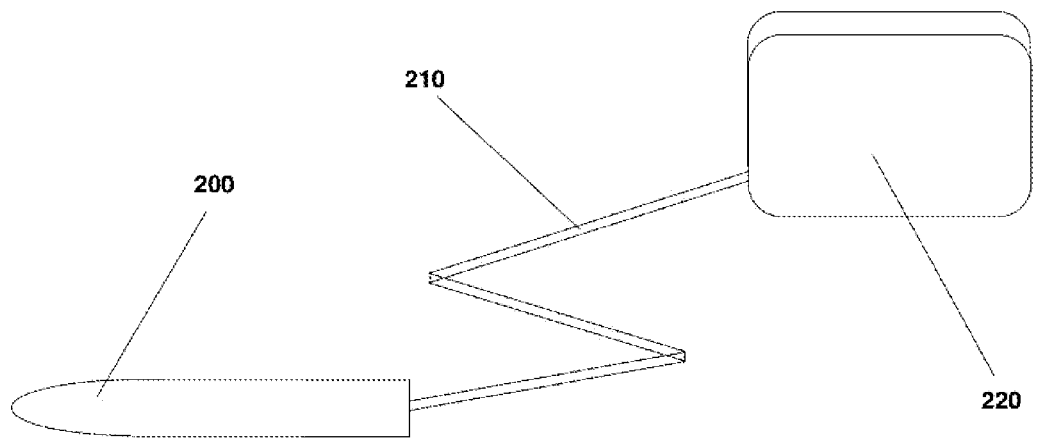
FIG. 2 shows a perspective view of the vaginal device of the present invention including the probe and external electronics box.
Figure 3:
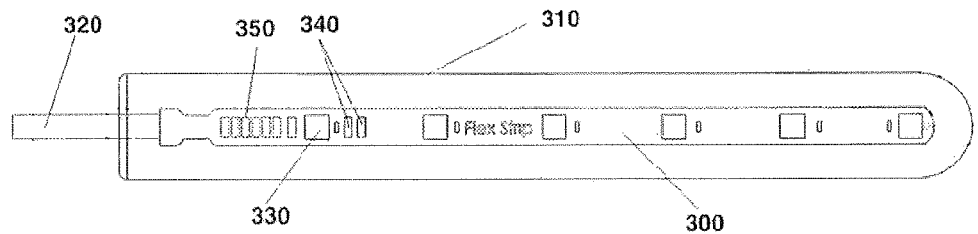
FIG. 3 shows a cross section view of the probe of the vaginal device of the present invention, including the flex strip.

FIG. 2 shows the elements of the system worn by the patient 100. The vaginal device may include a probe 200 that may be inserted into the vagina with cable 210 connecting the probe 200 to the external electronics box 220. FIG. 3 illustrates the probe of the vaginal device 310 with its internal electronics 300 and cable 320 extending to the external electronics box attached to electrical pads 350. MEMS accelerometers 330 may be mounted on a flex-strip circuit 300. ESD suppressors 340 may be on the same side of the strip as the MEMS accelerometers; the pads for connections to the thermistors for temperature measurement (not shown) are on the opposite of the flex strip 300. Pressure sensors may be included as well but are not shown in the figure. In one embodiment, the output from the MEMS accelerometers 350 uses I²C communications. The output of the thermistor may be processed through an analog-to-digital converter; thus outputs from both types of sensors may be translated into a transmittable digital signal.

Figure 4:
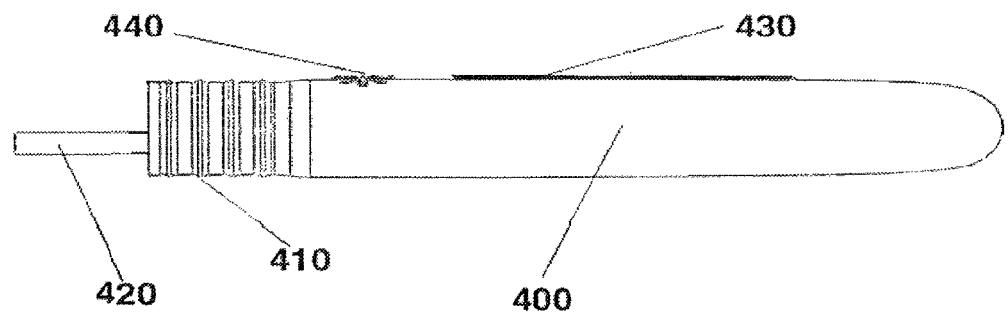
FIG. 4 shows a schematic view of the probe of the vaginal device of the present invention.

FIG. 4 shows a diagram of the side view of the probe of the vaginal device 400 with ribs 410 allowing patients to better grip the device 400 during insertion and possibly during removal (although the vaginal device is normally removed by pulling on cable 420 that extends to the external electronics box). In some embodiments, the probe may be composed of a silicone-material. The orientation line 430 may be disposed on the outer surface of the probe of the vaginal device 400. The logo 440 may be disposed on the outer surface of the probe of the device 400 as well. The logo 440 and line 430 may be molded into the silicone. The dimensions of the probe of the vaginal device 400 may typically be 16 mm in diameter and 11 cm long, usually in the range of 14 to 20 mm in diameter and 9 to 12 cm long.

Figure 5:
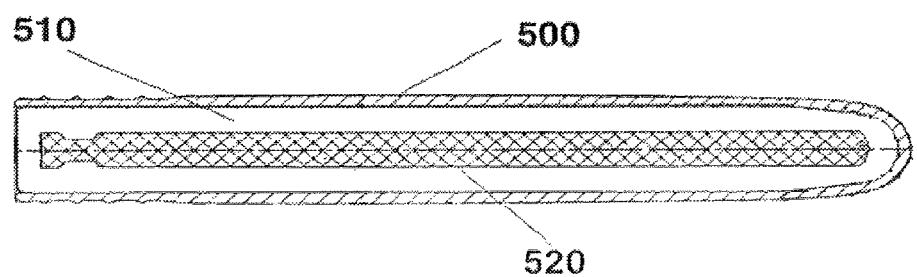
FIG. 5 shows a plan view of the probe of the vaginal device of the present invention.

FIG. 5 illustrates a plan view of the probe of the vaginal device. The probe of the vaginal device 500 is shown such that the outer silicone shell is shown as crosshatched. The electronics may reside on flexible strip 520 that is also shown as crosshatched. In one embodiment according to the present invention, the inner silicone portion 510 may be composed of two half cylinders of silicone, one above strip 510 and one below.

Figure 6:
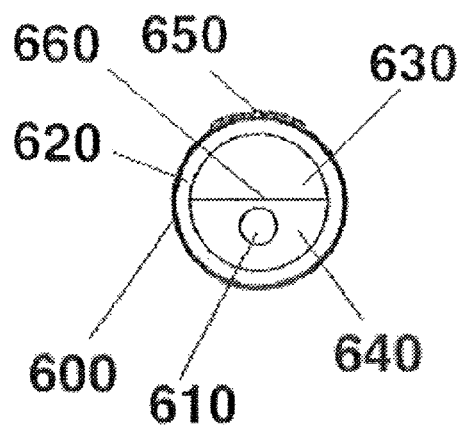
FIG. 6 shows a cross section view of part of the vaginal device of the present invention.

A cross section of the vaginal device 600 looking from the end from which cable 610 comes out is shown in FIG. 6. Silicone sheath 620 surrounds the upper silicone cylinder 630 and lower silicone cylinder 640 divided by separation line 660. The flexible strip may be sandwiched between the upper 630 and lower 640 cylinders positioned at separation line 660.

The vaginal device was designed with manufacturability as a key consideration. A critical element is that molding the silicone with the electronics enclosed takes too long a time to cure because the electronics used have a maximum temperature of 65° C. Short enough curing time to make such molding commercially practical requires the liquid silicone to be heated to on the order of 175° C. One manufacturing approach therefore was to mold upper cylinder half 630, lower cylinder half 640, and silicone sheath 620 at the higher temperature. The flexible electronics strip may then be placed on an upside-down upper cylinder half 630 with the MEMS accelerometers fitting into pockets in its surface placed by the mold tooling. The upside-down lower cylinder 640 may be coated with adhesive and then placed over the upside-down upper cylinder 630 tooling. Once the whole cylinder is assembled, the silicone sheath 620 may be placed into a fixture that applies vacuum to its sides and enlarges the opening. The full cylinder containing the sandwiched flexible electronics strip may then be inserted into the opening of the silicone sheath until the end of the full cylinder hits the end of sheath 620. The vacuum may then be released and the cylinder is suitably enclosed within the sheath. The wall of sheath 620 may be longer than the length of the cylinder. This is done so there will be a pocket surrounding cable 610 that when filled in with silicone material (Dow Silastic) that adheres to the silicone cylinder, the silicone sheath and the cable. All of the silicone materials are biocompatible. The cable jacket may be biocompatible or coated with a layer of Parylene or other coating that is biocompatible.

Figure 7:
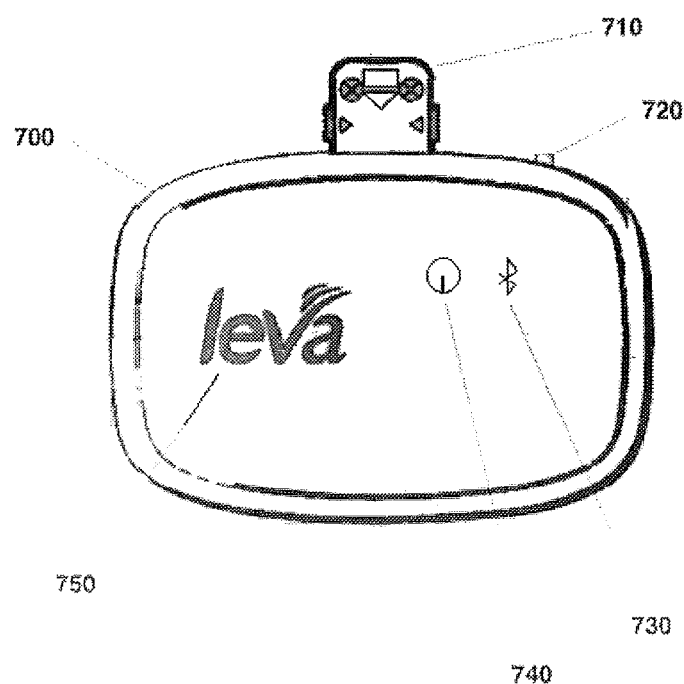
FIG. 7 is a view illustrating the external electronics enclosure of the present invention.

FIG. 7 illustrates the external electronics box 700, with logo 750 that receives its data input from connector 710 with its cable to the vaginal device. The external electronics box may be turned on by power button 720. A BLUETOOTH® indicator Light-Emitting Diode (LED) 730 and System-indicator LED 740 signal status may also be included as part of the external electronics box.

Figure 8:
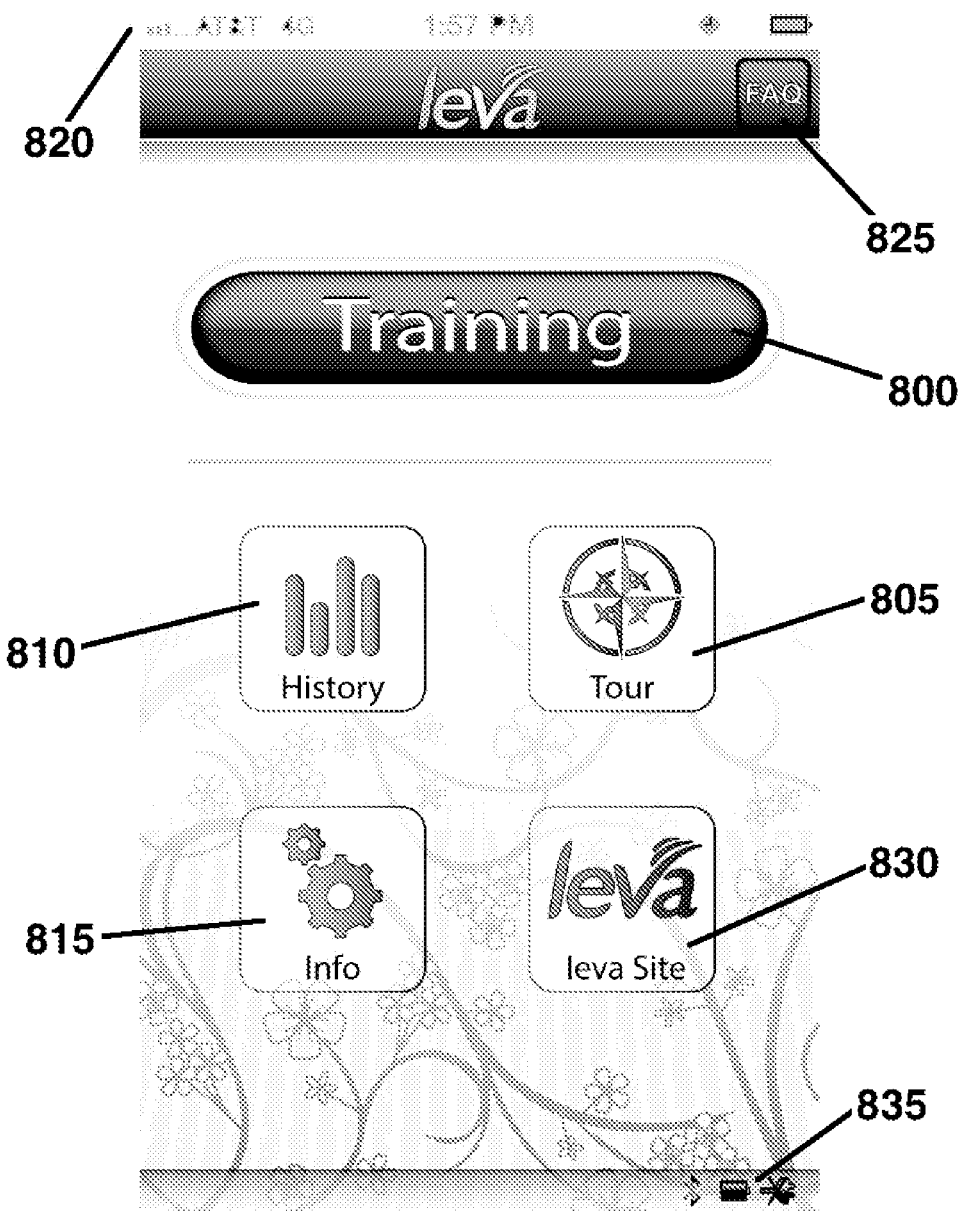
FIG. 8 is a view illustrating the Application Main Screen of the present invention.

External electronics box 700 in FIG. 7 communicates wirelessly via e.g., BLUETOOTH® to a smart device such as an IPHONE®. One embodiment of the external electronics box 700 is the LEVA® device for the prevention and treatment of pelvic dysfunction including urinary incontinence. FIG. 8 shows the main-menu screen of the smart device. A splash screen (not shown) may precede the main-menu screen. The user may log in to get access to the application on the smart device. An operative button on the screen is Training button 800. Other buttons are the Tour 805, History 810, Info 815, and LEVA® site 830. Tour 805 provides access to screens giving background on the application. Info 815 provides access to the information such as the identification of the LEVA® device to which the smart device is connected. Button 810 provides access to the history of the patient's sessions. This is shown in further detail in FIG. 15 below. The first bar 820 located at the top of the screen includes, from left to right, the mobile-phone signal levels, the network operator (in this case AT&T) the type of communications (LTE in this case), an active Wi-Fi Internet connection (if any, not present in this case) the time, the fact an alarm is set, the BLUETOOTH® communication is active, and the battery is fully charged. Button 825 provides access to the FAQs (if Internet connection is available). The second bar 835 located at the bottom of the screen, from left to right shows that there is a BLU-ETOOTH® connection to the LEVA® device, the battery of the LEVA® device is charged, and that the LEVA® device is not plugged in.

Figure 9:
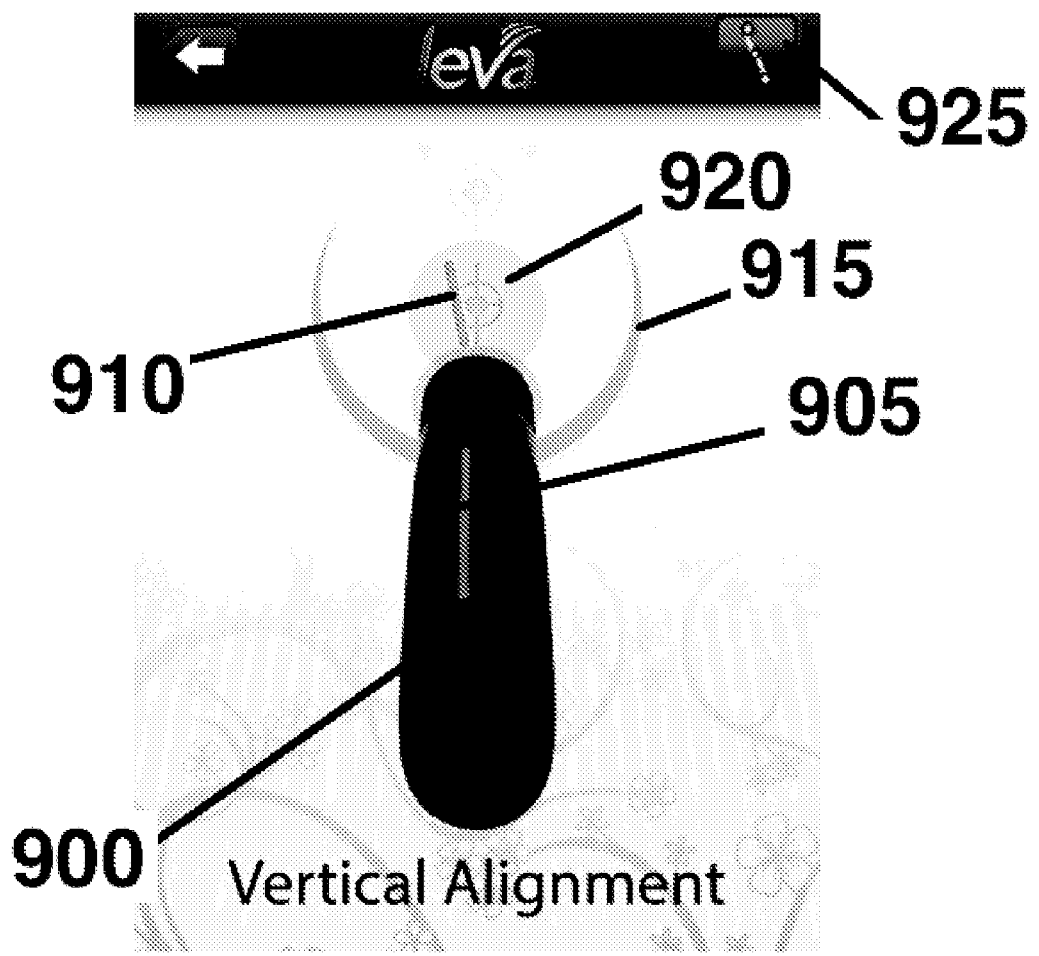
FIG. 9 is a view illustrating the Vertical Alignment Screen of the present invention.

FIG. 9 illustrates the screen that allows the patient to see whether she has orientated the LEVA® device properly, namely the device 900 is oriented with its top at the "twelve o'clock" position with the orientation line 905 directly towards the patient's anterior. Relative orientation 910 in this case shows the LEVA® device is rotated slightly counter clockwise relative to target 920. Circle-with-arrows 915 indicates to the patient which direction to physically rotate the device to move it into proper orientation. Icon 925 indicates that the application is in line mode as shown in further detail in FIG. 10. The training session cannot begin until vaginal device is correctly aligned.

Figure 10:
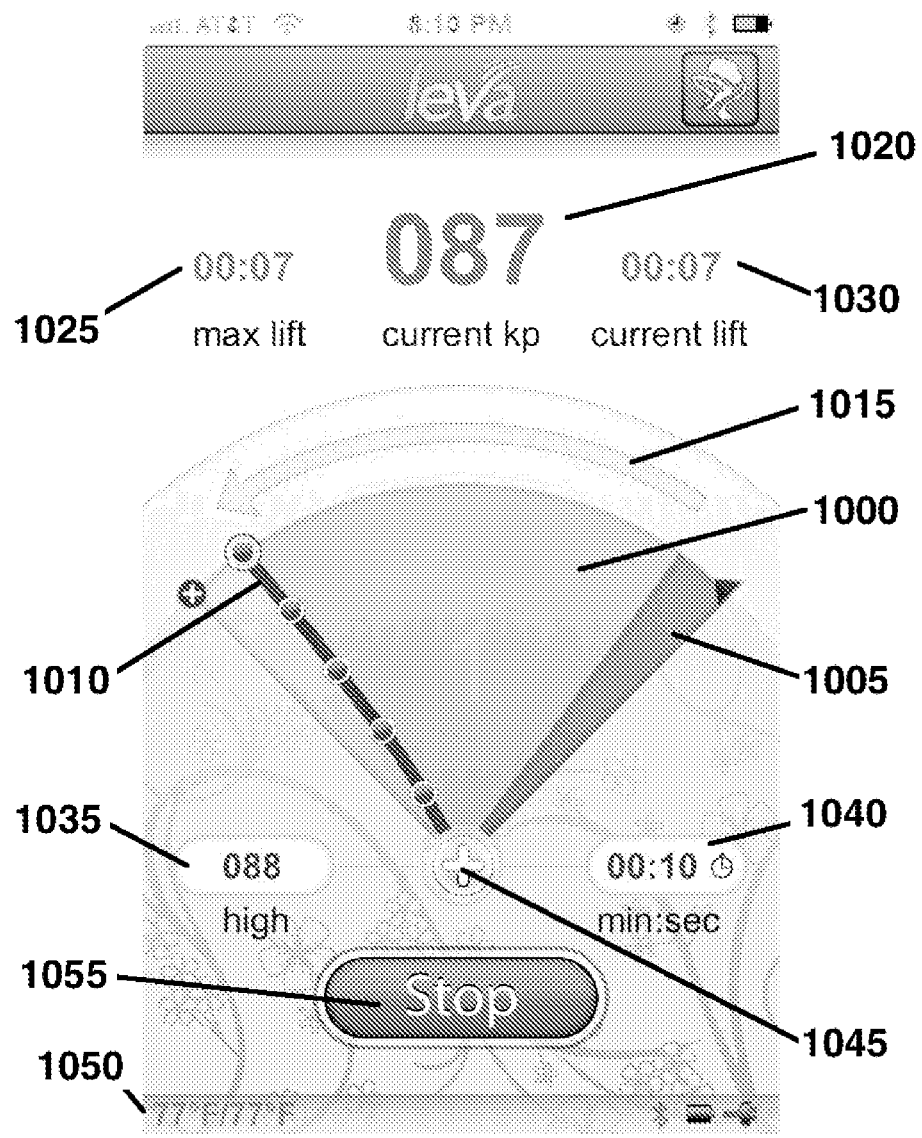
FIG. 10 is a view illustrating the Training Screen (Zoom 1 kp 087) of the present invention.

FIG. 10 shows the training screen in dynamic-line mode. Background 1000 indicates the area of motion of dynamic line 1010 where line 1010 represents the profile of the vaginal device within the vagina. The dots on the line show the positions of the six MEMS accelerometers on the flexible strip. Area 1005, with the red background, is where line 1010 will be displayed if one is bearing down as if one were having a bowel movement. Thus it is possible to differentiate between a correct and incorrect Kegel exercise. Line 1010 will appear in region 1005 if the attempt to do a Kegel exercise is incorrect. Arrow 1015 illustrates the proper direction for a correct Kegel exercise. As noted above, however, area 1005 may be the desired location of line 1010 in the case where the patient is getting into a relaxed state in connection with the relief of pelvic pain. The right-to-left movement of line 1010 is referred to as a lift. The Kegel exercise unit may be the Kegel power abbreviated kp, although other designations can be used. Current kp 1020 in FIG. 10 is 087 (87, since leading zeros are ignored). The greater the lift of the vaginal device towards the anterior of the patient, the higher the kp score. The maximum length of time the lift was held 1025 during the session in the figure is 00:07 or seven seconds. The length of time that the current lift is held 1030 is also seven seconds in this example. The value for the highest value of kp score in the current session 1035 is 088. The time for the current session 1040 is 10 seconds. To zoom in so the highest score displayed in the region is not 100, but less, the user clicks on the plus sign 1045. Zoom level is displayed on the screen background 1000. Background 1000 maybe filled with blue color to indicate the maximum score during the session. The temperature of the vaginal device near the entrance to the vagina is 1050 with the first value (77° F.) being the current temperature and the second is the maximum temperature in the session (also 77° F. in this example). To stop the session, the user may press the stop button 1055.

Figure 11:
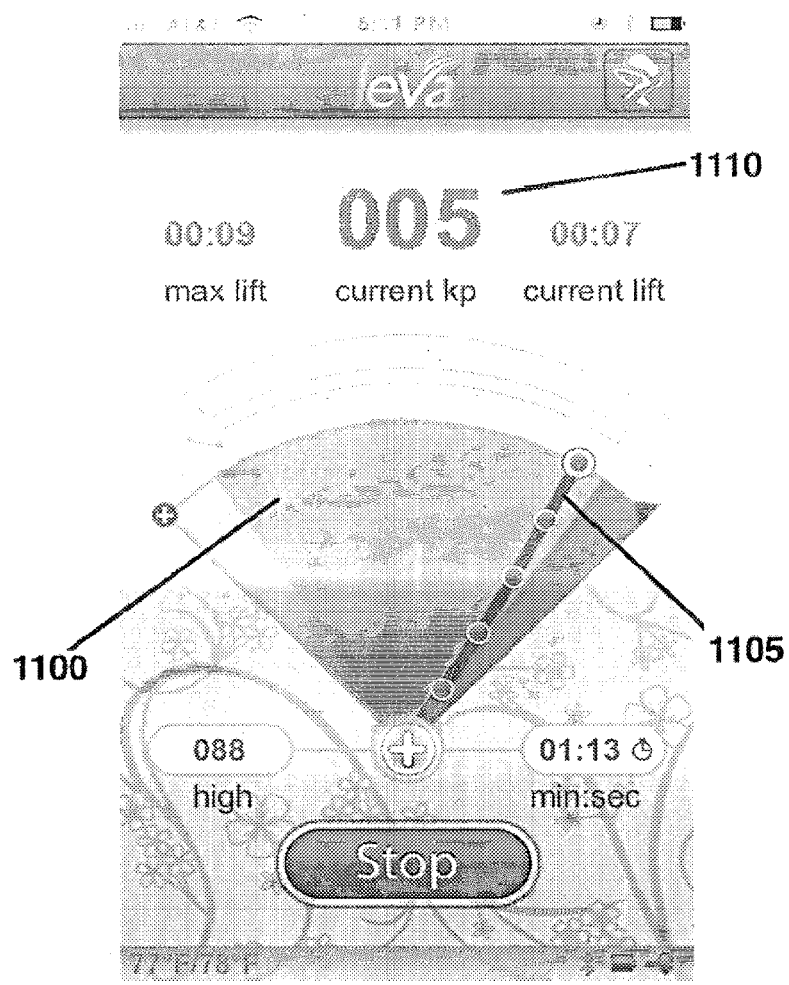
FIG. 11 is a view illustrating the Training Screen (Zoom 1 kp 005) of the present invention.
Figure 12:
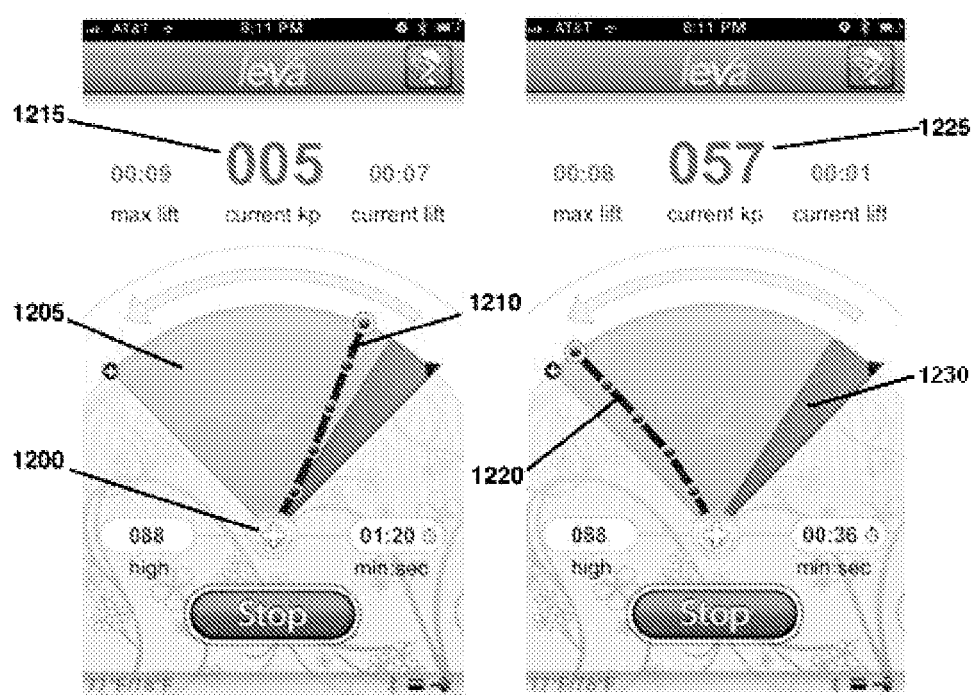
FIG. 12(A) is a view illustrating the Training Screen (Zoom 2 kp 005) of the present invention.
FIG. 12(B) is a view illustrating the Training Screen (Zoom 2 kp 057) of the present invention.

FIG. 11 shows an example of the training screen in Zoom 1 mode with a kp score 1110 (005) on background field 1100. Zoom 1 covers the display range of 0 to 100. If the line does not move much when a patient tries to do a Kegel exercise, the patient may get discouraged. The application provides the facility to "zoom in" and display scores in the range of 0 to approximately 60 for Zoom 2 and 0 to approximately 30 for Zoom 3. The red zone 1230 at the right edge of overall background is zoomed as well. Zooming in changes the amount that the dynamic line will move for a given degree of lift, but does not change the score. FIG. 12 illustrates two examples of Zoom 2. One may change the zoom level by Zoom button 1200, alternating among the three zoom levels. In FIG. 12A, background 1205 shows the application is set to zoom level 2, with line 1210 at the level of five kp as reflected in the digital score 1215 of 005. Another example of Zoom 2 is shown in FIG. 12B. In this case, dynamic line 1220 is near the top of the range with score 1225 indicating a value of 057. In this example, line 1220 is curved reflecting the physical profile of the MEMS accelerometer along the flexible strip contained within the vaginal device. The kp score does not change based on the zoom. The maximum score is maintained within a session if the zoom level is changed. If the user generates a score higher than the maximum for that zoom level, "—" is displayed rather than a numeric score.

Figures 13A, 13B:
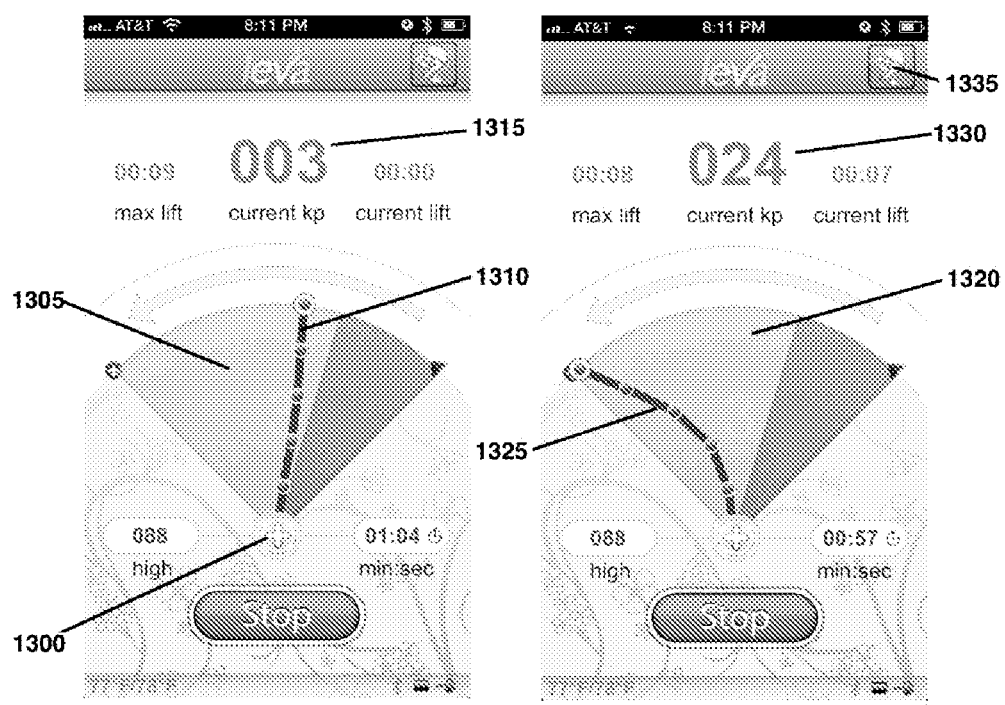
FIG. 13 (A) is a view illustrating the Training Screen (Zoom 3 kp 003) of the present invention.

FIG. 13 illustrates a pair of examples of Zoom 3. Again one changes the zoom level by Zoom button 1300, again alternating among the three zoom levels. In FIG. 13A, background 1305 shows the application is set to zoom level 3, with line 1310 at the level of three kp as reflected in the digital score 1315 of 003. Another example of Zoom 3 is shown in FIG. 13B. In this case, region 1320 again shows Zoom 3, and line 1325, is toward the top of the range with score 1330 indicating a value of 024. In both FIGS. 13A and 13B the lines 1305 and 1325 are curved representing the physical profile of the vaginal device. Icon 1335 indicates the anatomy-mode choice that can be selected.

Figure 14:
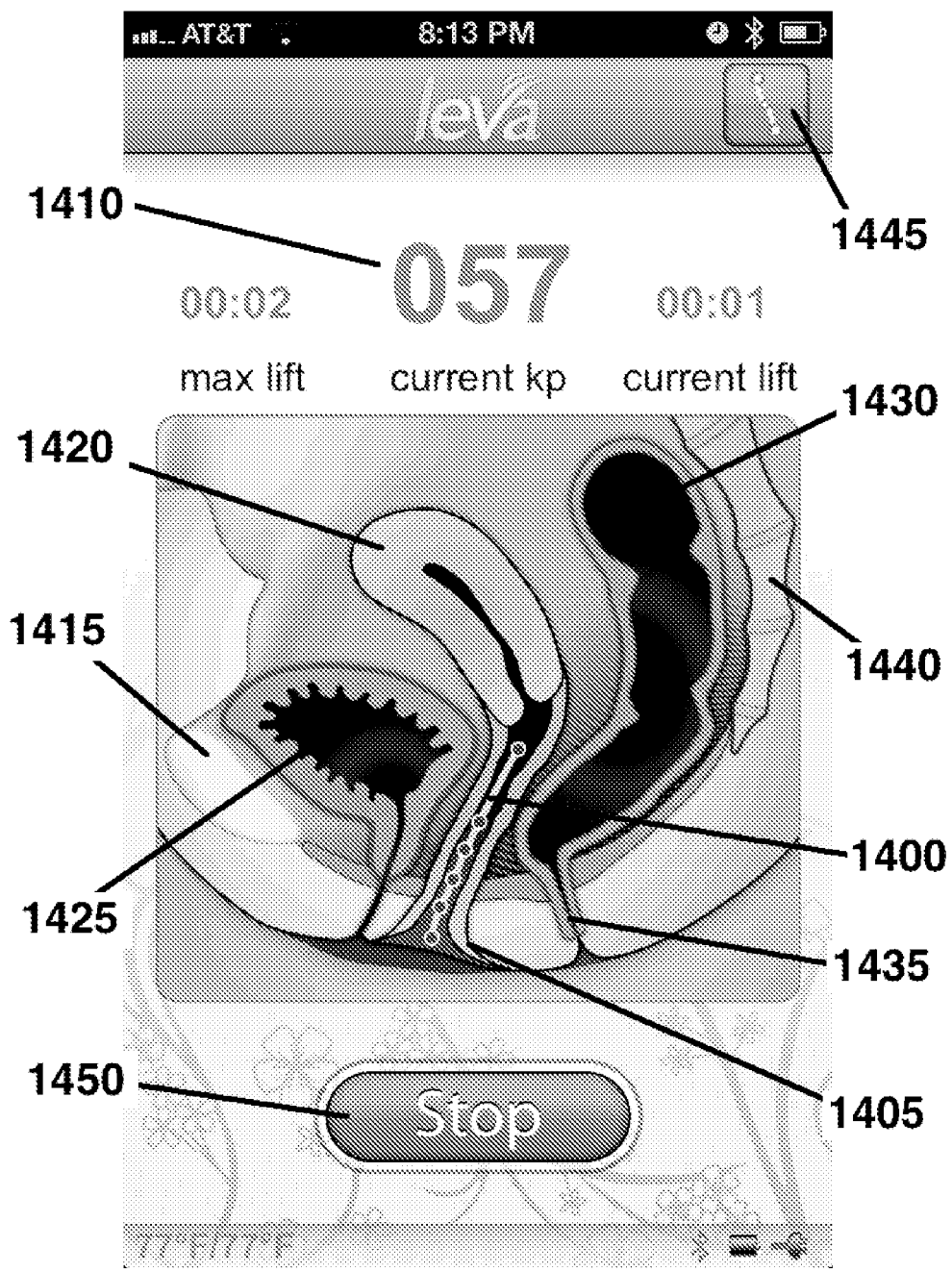
FIG. 14 is a view illustrating the Anatomical Animation of the present invention.

FIG. 14 illustrates the training session using an anatomical animation to display lift as opposed to the dynamic line. To access this mode, the user may touch the anatomy icon at the top right of the Training screen when in dynamic-line mode (e.g., icon 1335 in FIG. 13B). Line 1400 moves with the Kegel contraction, but is not necessarily scaled to score 1410, in this case 057. The pelvic organs shown are pubic bone 1415, uterus 1420, bladder 1425, colon 1430, anus 1435, and coccyx 1440. Some of these organs move on the display as the Kegel is executed. To end the training session, the patient may press the Stop button 1450. To access the dynamic-line mode, the patient may touch the dynamic-line-mode icon 1445.

Figure 15:
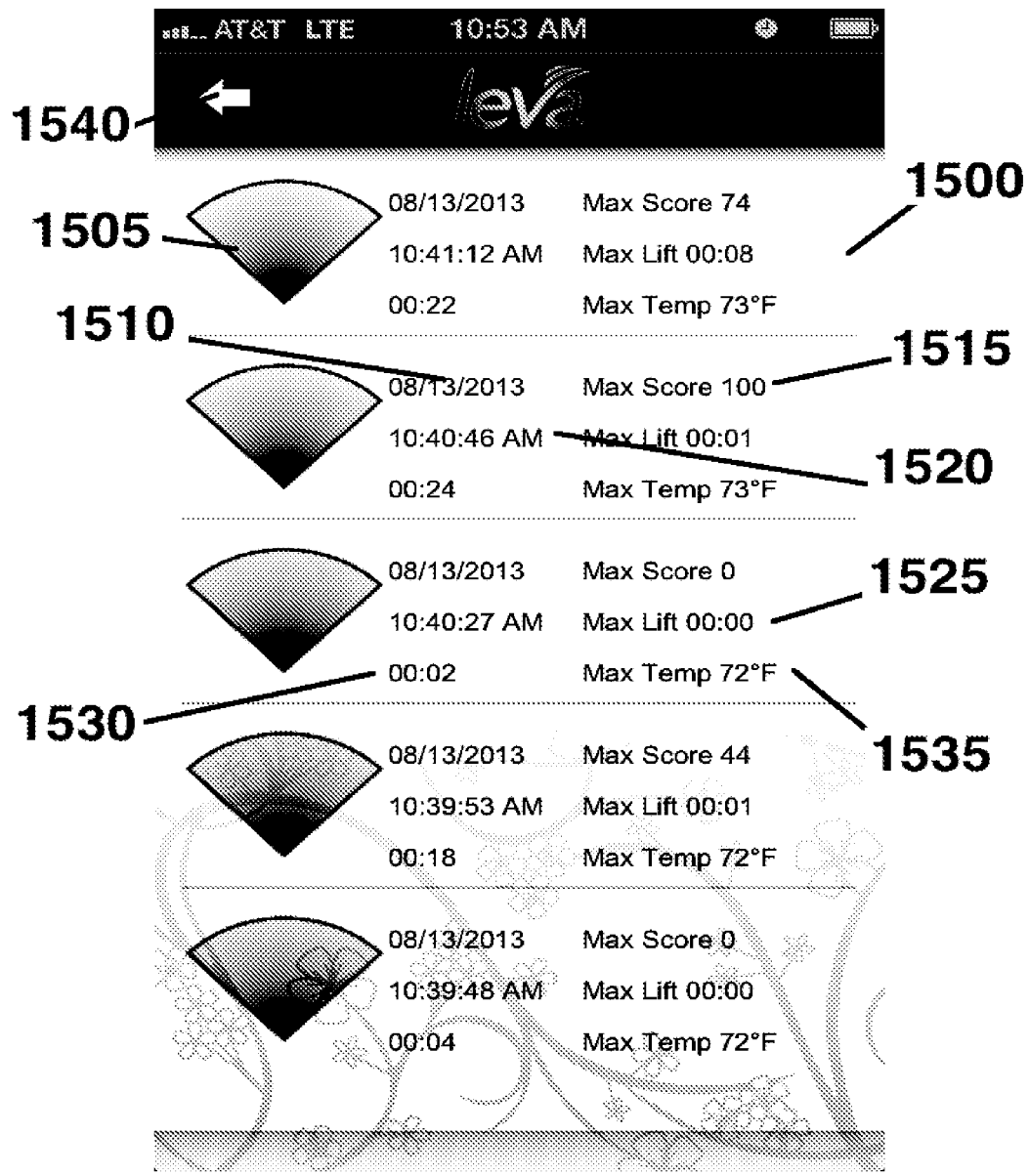
FIG. 15 is a view illustrating the History Screen of the present invention.

FIG. 15 shows the History screen. This element of the App may be accessed through the Menu screen shown in FIG. 8. The readings for each session may be contained within a region 1500, with icon 1505. Readings may be session date 1510, maximum score 1515, session time 1520, maximum lift time 1525, session-duration time 1530 and maximum temperature 1535. To return to the Main Menu screen, FIG. 8, one touches return arrow 1540.

When a session is closed, the data may be kept both in a file on the smart device uploaded to a database on the central database server. The user does not need to take any action for the latter to happen. If the smart device does not have an Internet connection at the time a given session is closed, the data for that session may be uploaded at a later time when both the application is being used and an Internet connection is available. Those with access authorization may access the data in the database. Such users may be the patient, the healthcare provide taking care of them, third party payers, or central customer support personnel in some circumstances. The patient must give authorization for the various uses of the information. The patient may view her history on the smart device or on a web browser. The healthcare professional via a web browser may provide a prescription for the patient (e.g., how many sessions per day and length of each session) placed in the central database. The patient using a web browser may access that prescription. In another embodiment, the patient may keep a diary on the smart device and that diary information is uploaded to the central database and accessible by the patient and authorized healthcare professionals.

The invention supports the patient. The process begins with a healthcare professional training the patient in the use of the LEVA® device. The patient may receive feedback from the LEVA® device on how well she is doing her Kegel exercises. Proper performance of the Kegel exercises may provide for prevention or mitigation of pelvic dysfunction including urinary incontinence, fecal incontinence, pelvic pain, and pelvic-organ prolapse. Proper performance of Kegels may also result in improvement of sexual experience. With permission of the patient, data from the sessions may be shared with the healthcare professional(s) taking care of the patient either through the web-based database or by the patient bringing in their LEVA® device. For third-party payments, the web-based database data may be available to authorized third parties.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention.

What is claimed is:

1. A system for optimizing a patients pelvic floor muscle exercise comprising:
   a user interface device comprising a graphical user interface that is configured to run a computer implemented application comprising visual and/or auditory feedback features; and
   an intravaginal device comprising a plurality of accelerometers positioned along a length of the device, wherein the intravaginal device is sized for insertion into the patient's vagina and generates signals in response to movement of the accelerometers;
   wherein the user interface device is wirelessly connected to the intravaginal device and is configured to receive and analyze the signals from the intravaginal device using the application;
   wherein the application is configured to:
      display a positional image comprising a line on the graphical user interface that corresponds to the position of the patient's vagina that is generated by the accelerometers of the intravaginal device during performance of the pelvic floor exercise, wherein the positional image corresponds to a lift maneuver when the line rotates from right to left and wherein the positional image corresponds to a bearing down movement when the line rotates from left to right;
      display and record a change in indicia over time, wherein the indicia correspond to the positional image that is generated by the accelerometers prior to and during performance of the pelvic floor exercise, and wherein the recorded indicia further comprise a session date, session time, maximum lift time, and session duration time; and
      provide physiological feedback information to the patient using the visual and/or auditory feedback features based on a change in the positional image over time and a duration of time during which the positional image reflects performance of the lift maneuver,
   wherein the physiological feedback information and the recorded indicia encourage the patient to:
      i) activate pelvic floor muscles in a manner that strengthens the pelvic floor;
      ii) limit activation of pelvic floor muscles in a manner that harms the pelvic floor; and
      iii) increase the duration of time during which activation of the lift maneuver of the pelvic floor muscles that strengthen the pelvic floor is maintained, thereby optimizing the pelvic floor muscle exercise.

2. The system of claim 1, wherein the user interface device further comprises a data processor and a communication module configured to store and retrieve Cloud-based patient data remotely.

3. The system of claim 2, wherein the physiological feedback information is a visual or numerical display of the patients pelvic floor muscle exercise history, which is retrieved as part of the Cloud-based patient data.

4. The system of claim 1, wherein the physiological feedback information is a visual or numerical display of Kegel power.

5. The system of claim 1, wherein the physiological feedback information is a visual or numerical display of pelvic floor muscle exercise optimization.

6. The system of claim 1, wherein the user interface device is connected to the intravaginal device through wireless short-range radio wave communication.

7. The system of claim 1, wherein the user interface device is selected from the group consisting of a smartphone, tablet, and watch.

8. The system of claim 1, wherein the intravaginal device comprises six accelerometers.

9. The system of claim 1, wherein the feedback comprises an auditory and/or vibratory signal.

10. The system of claim 1, wherein the visual and/or auditory feedback is configured to indicate if the intravaginal device is orientated properly.

11. The system of claim 1, wherein the recorded indicia are stored in a diary on the user interface device.

* * * * *

UNITED STATES PATENT AND TRADEMARK OFFICE
CERTIFICATE OF CORRECTION

| | |
|---|---|
| PATENT NO. | : 11,426,625 B2 |
| APPLICATION NO. | : 15/109807 |
| DATED | : August 30, 2022 |
| INVENTOR(S) | : Ramon Jose Iglesias et al. |

It is certified that error appears in the above-identified patent and that said Letters Patent is hereby corrected as shown below:

In the Claims

Column 9, Line 35, replace "patients" with --patient's--.

Column 10, Line 33, replace "patients" with --patient's--.

Signed and Sealed this
Twenty-first Day of March, 2023

Katherine Kelly Vidal
*Director of the United States Patent and Trademark Office*